(12) United States Patent
Drennan et al.

(10) Patent No.: US 11,311,231 B2
(45) Date of Patent: Apr. 26, 2022

(54) DRESSING ASSEMBLY

(71) Applicant: Walgreen Health Solutions, LLC, Lake Forest, IL (US)

(72) Inventors: Denis Burke Drennan, Evanston, IL (US); Matthew Frank Trapani, Deerfield, IL (US)

(73) Assignee: Walgreen Health Solutions, LLC, Lake Forest, IL (US)

(*) Notice: Subject to any disclaimer, the term of this patent is extended or adjusted under 35 U.S.C. 154(b) by 385 days.

(21) Appl. No.: 15/084,409

(22) Filed: Mar. 29, 2016

(65) Prior Publication Data

US 2017/0281073 A1 Oct. 5, 2017

(51) Int. Cl.
*A61B 5/00* (2006.01)
*A61F 13/02* (2006.01)
*A61F 15/00* (2006.01)
*A61B 5/0531* (2021.01)
*A61F 13/00* (2006.01)
*G16H 40/67* (2018.01)
(Continued)

(52) U.S. Cl.
CPC .............. *A61B 5/447* (2013.01); *A61B 5/002* (2013.01); *A61B 5/0022* (2013.01); *A61B 5/0051* (2013.01); *A61B 5/0053* (2013.01); *A61B 5/053* (2013.01); *A61B 5/0531* (2013.01); *A61B 5/445* (2013.01); *A61B 5/6829* (2013.01); *A61B 5/6832* (2013.01); *A61B 5/6892* (2013.01); *A61B 5/742* (2013.01); *A61B 5/7405* (2013.01); *A61B 5/746* (2013.01); *A61B 5/7455* (2013.01); *A61F 13/00051* (2013.01); *A61F 13/02* (2013.01); *A61F 13/0243* (2013.01); *A61F 13/0253* (2013.01); *A61F 13/0256* (2013.01); *A61F 15/008* (2013.01); *G16H 40/67* (2018.01); *A61B 5/0082* (2013.01); *A61B 5/026* (2013.01); *A61B 5/442* (2013.01); *A61B 2560/0214* (2013.01); *A61B 2560/0412* (2013.01); *A61B 2562/0233* (2013.01); *A61B 2562/0247* (2013.01); *A61B 2562/0271* (2013.01); *A61B 2562/04* (2013.01); *A61B 2562/12* (2013.01); *A61B 2562/187* (2013.01); *A61B 2562/247* (2013.01)

(58) Field of Classification Search
CPC ...... A61B 5/447; A61F 13/02; A61F 13/0243; A61F 13/0256
USPC .................................. 600/504, 549
See application file for complete search history.

(56) References Cited

U.S. PATENT DOCUMENTS 5,109,849 A * 5/1992 Goodman .............. A61B 5/252
600/483
8,903,467 B2 * 12/2014 Sweitzer .............. A61B 5/0002
600/324

(Continued)

*Primary Examiner* — Daniel L Cerioni
*Assistant Examiner* — Raymond P Dulman
(74) *Attorney, Agent, or Firm* — Hartman Global IP Law; Gary M. Hartman; Domenica N.S. Hartman

(57) ABSTRACT

A dressing assembly for providing a warning to a patient or caregiver that the patient needs attention. The dressing assembly is adapted to be applied to or near a surface of the patient's body and generate electrical outputs corresponding to soft tissue pressure and other health characteristics sensed at the surface. The dressing assembly includes a pocket formed therein for removable, secured and protected insertion of a variety of different sensors such as multiple pressure sensors.

11 Claims, 6 Drawing Sheets

(51) Int. Cl.
*A61B 5/053* (2021.01)
*A61B 5/026* (2006.01)

(56) References Cited

U.S. PATENT DOCUMENTS

| | | | | |
|---|---|---|---|---|
| 2003/0149349 | A1* | 8/2003 | Jensen | A61B 5/02055 600/372 |
| 2005/0148904 | A1* | 7/2005 | Mimura | A61B 5/1126 600/587 |
| 2005/0245839 | A1* | 11/2005 | Stivoric | G06F 19/00 600/549 |
| 2010/0113999 | A1* | 5/2010 | Lam | A61L 15/425 602/79 |
| 2011/0308019 | A1* | 12/2011 | Terawaki | A61G 7/05769 5/713 |
| 2012/0109083 | A1* | 5/2012 | Coulthard | A61F 13/02 604/319 |
| 2013/0232761 | A1* | 9/2013 | Warren | A61F 13/0276 29/428 |
| 2013/0245582 | A1* | 9/2013 | Croizat | A61M 1/0088 604/319 |
| 2013/0331823 | A1* | 12/2013 | Askem | F04B 49/06 604/543 |
| 2016/0038345 | A1* | 2/2016 | Ha | A61F 13/02 602/46 |

* cited by examiner

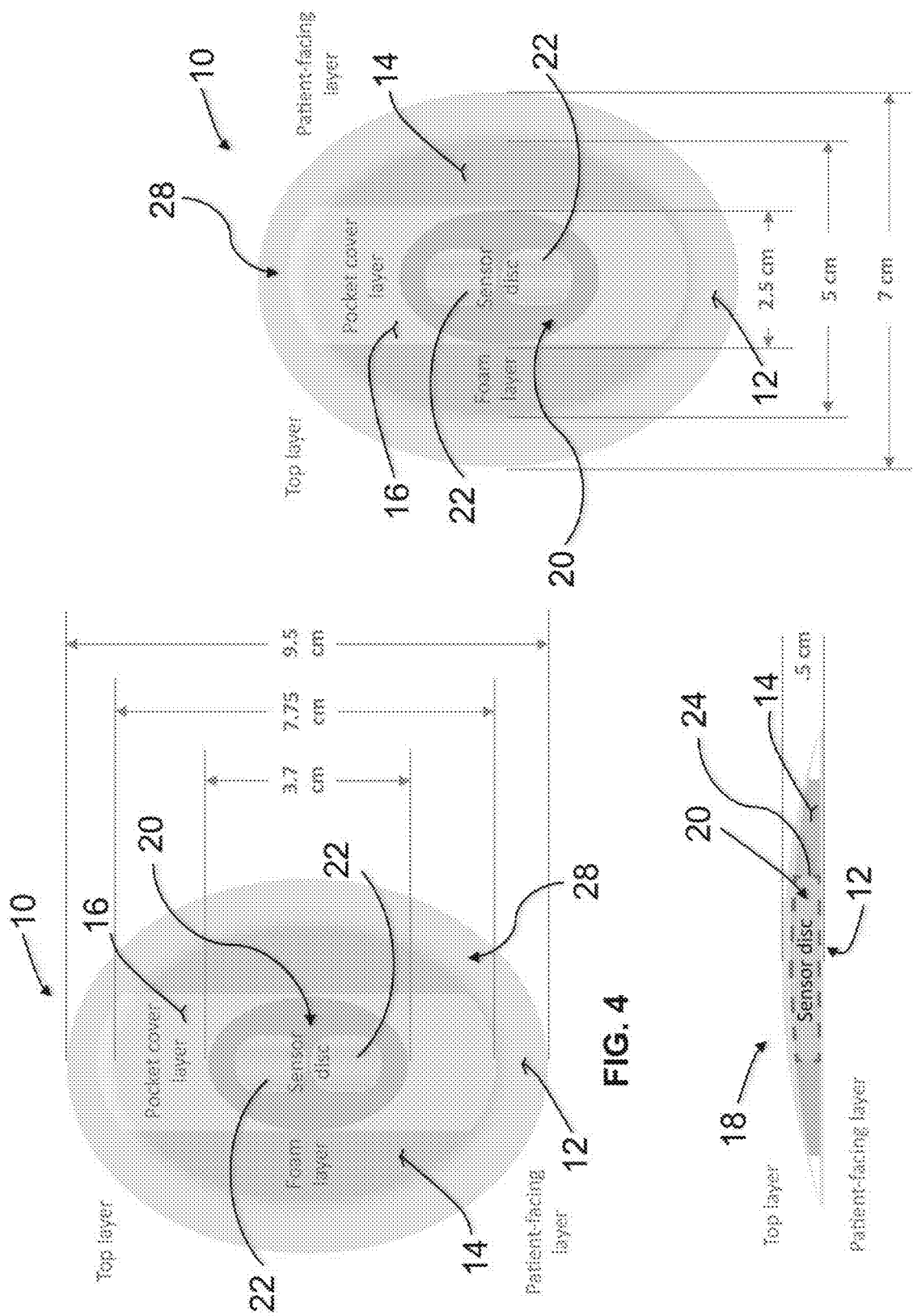

DRESSING ASSEMBLY

BACKGROUND OF THE INVENTION

The present invention generally relates to equipment for use with health care patients. More particularly, the present invention encompasses a dressing system that includes sensors for monitoring soft tissue pressure and other characteristics on any existing wounds, skin areas at high risk for pressure ulcers or post-surgery care and other ailments that require sensing to enable any kind of body healing.

Pressure (decubitus) ulcers, commonly known as bedsores, present a serious problem to bedridden and wheelchair-confined patients. Prolonged pressure from a patient's body weight upon a bony prominence is the most common cause of pressure ulcers. Prevention of and care for a preexisting pressure ulcer typically include treatment plans that involve relieving pressure on the exposed area by positioning and maintaining the patient off susceptible areas and any preexisting pressure ulcers, and minimizing localized pressure through the use of gel pads and similar types of products capable of absorbing and/or distributing pressure. However, such approaches can be insufficient if caregivers are unaware that a patient has shifted his/her weight onto prominences and sensitive areas that are prone to pressure ulcers.

There are a wide variety of pressure sensors in the industrial and medical markets, some of which have found use in monitoring pressure ulcers. Notable examples include those that use air and fluid displacement techniques, as well as electromechanical analog devices. Many of these sensors are very portable and can be used to measure pressures at various locations of a patient at any point in time. There are also sheets of pressure sensors used primarily for research that give color-coded results from computer programs. The latter sensor type has been particularly used by manufacturers and some healthcare facilities to identify maximum tissue pressures under bed and wheelchair patients' skin areas. There are also a number of pressure monitoring devices, for example, the Oxford Pressure Monitor MKII with 12 Sensor system available from the Talley Group, Ltd., and the Pressore Alert system available from Cleveland Medical Devices, Inc.

Conventional dressing assemblies that are frequently used with pressure sensors include a simple multilayer construction dressing with a sensor embedded there between. These conventional dressing assemblies are hardwired using a connection cable connected to the dressing on one end of the cable and to a controller on the other end of the cable. The controller is strapped to a bed to monitor a patient and alert a patient or caregiver that soft tissue pressure has exceeded some predetermined level that over time. These dressing assemblies are often impaired in their effectiveness because such dressings do not adequately secure the sensor in position especially if the patient is frequently shifting their position in bed and the dressing is tethered to the controller. Therefore, the construction of the dressing assembly is often based on trying to reduce the thickness profile of the dressing as much as possible to decrease the possibility of the dressing shifting as the patient moves into a different position and is connected to the controller. While a very thin dressing assembly may be more effective in this wired configuration, patient comfort is often sacrificed thereby resulting in patients trying to reposition the dressing assemblies themselves to become more comfortable or the sensor itself may cause undue pressure on the skin if it is not adequately cushioned within the dressing.

Additionally, the majority of the dressing assemblies offer a broad variety of materials of different characteristics intended to assist with wound healing. Most of these dressings are designed to prevent wound contamination. They are not designed to adhere a pressure sensitive wireless continuous transmitting device/sensor to skin surfaces or any device of any thickness to monitor patient vital signs.

What is needed in the art is a pressure monitoring dressing assembly that is no longer restricted by an attached cable wherein such dressing assembly is comfortable which actually increases the effectiveness of the monitoring of the pressure being applied to the skin. A novel pressure monitoring dressing assembly device is needed that is uniquely designed to function on different anatomical sites and be configured to accommodate a thickness able to disseminate the focal pressure of the sensor to prevent skin damage especially over bony prominences. Finally, a dressing is needed that provides reusable openings to allow for the removal and reinsertion of different sensors in order to more cost effectively reuse a sensor in new dressings.

SUMMARY OF THE INVENTION

The present invention provides a wireless pressure sensing dressing assembly as part of a system for providing a warning to a patient or caregiver that soft tissue pressure has exceeded some predetermined level that, over a sufficient period of time, would necessitate that the patient should move or be moved to prevent or at least reduce the risk of soft tissue damage. The dressing assembly may include an improved dressing configuration over existing dressing assemblies.

According to one aspect of the invention, the dressing assembly includes four primary layers—a patient facing layer, a foam layer, a pocket cover layer and a top layer. The patient facing layer that is preferably a transparent film dressing of silicon (or other type of material) membrane with a thin coat of adhesive on one side to permanently bind to additional layers. The patient facing layer is impermeable to liquid, water and bacteria but permeable to moisture vapor and atmospheric gases to provide maximum flexibility. The patient facing layer has one side with the reusable adhesive. The purpose of the patient facing layer is to attach the dressing to the skin of the patient or to attach the dressing to another dressing so that additional dressing layers can be attached directly to the patient facing layer. There are multiple layers of material in the preferred embodiment of the current invention of the dressing assembly wherein the patient facing layer is preferably the widest diameter layer amongst all of the layers in the dressing assembly.

According to another aspect of the invention, a pressure monitoring system provides a warning to a patient or caregiver that the patient should be moved to at least reduce a risk of soft tissue damage to the patient. The dressing includes a pressure-sensitive dressing assembly adapted to be applied on or near a surface of the patient's body that is susceptible to damage from soft tissue pressure.

The pressure-sensitive dressing assembly generates electrical outputs corresponding to soft tissue pressure sensed by the pressure-sensitive dressing assembly at the surface of the patient's body. The electrical outputs generated by the dressing assembly are monitored and an alarm is generated when the outputs from the dressing assembly exceed a predetermined pressure and time level.

Other aspects and advantages of this invention will be better appreciated from the following detailed description.

BRIEF DESCRIPTION OF THE DRAWINGS

FIG. 4 schematically represents components of a dressing assembly in accordance with the preferred aspect of this invention.

FIG. 5 schematically represents components of a dressing assembly in accordance with the preferred aspect of this invention.

FIG. 6 schematically represents a side view of a dressing assembly in accordance with the preferred aspect of this invention.

DETAILED DESCRIPTION OF THE INVENTION

Figure 2:
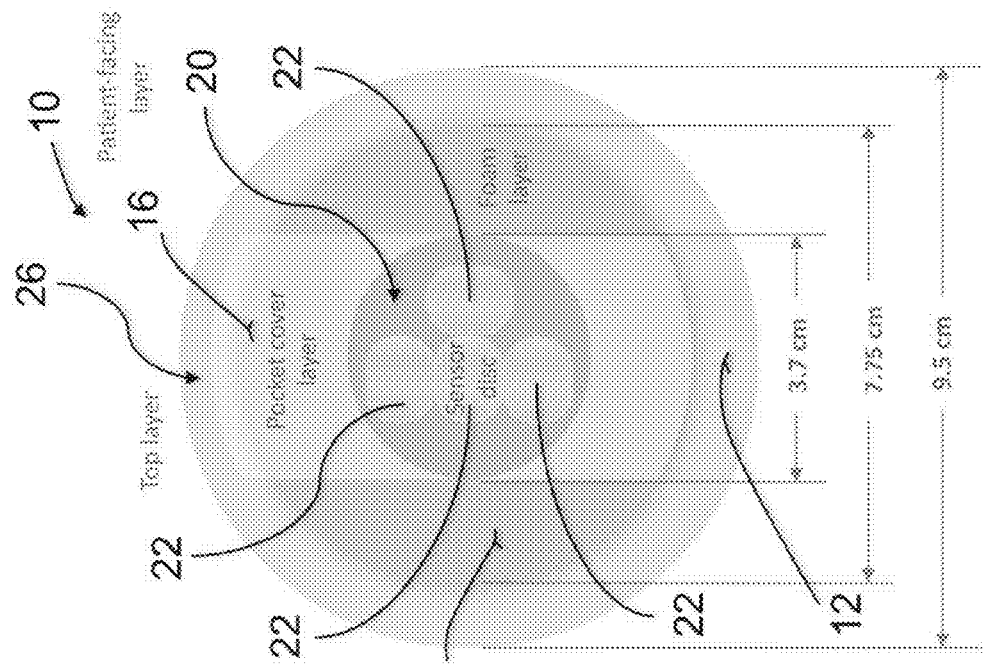
FIG. 2 schematically represents components of a dressing assembly in accordance with the preferred aspect of this invention.

Various features and advantages are explained more fully with reference to the non-limiting embodiments that are illustrated in the accompanying drawings and detailed in the following description. Descriptions of well-known starting materials, processing techniques, components and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions and/or rearrangements within the spirit and/or scope of the underlying inventive concept will become apparent to those skilled in the art from this disclosure.

In the following description, numerous specific details are provided, such as examples of material selections, dimensions, etc. to provide a thorough understanding of the present embodiments. Those skilled in the relevant art will recognize, however, that the invention may be practiced without one or more of the specific details, or with other methods, components, materials and so forth. In other instances, well-known structures, materials, or operations are not shown or described in detail to avoid obscuring aspects of the invention.

The present invention provides a dressing assembly as part of a pressure monitoring system whose primary function is to monitor a patient that is reclined or otherwise in a position that may result in the patient's weight applying pressure to an area of the patient's body that is susceptible to pressure ulcers, such as soft tissue overlying a bony prominence. The pressure monitoring system further operates to correlate soft tissue pressure levels with time to warn if an applied pressure has met certain pressure and time thresholds that, in combination, are likely to result in or exacerbate a pressure ulcer.

A variety of time periods may be utilized as suitable time thresholds (for example, ten, thirty, or sixty minutes) that can be selected by a caregiver. The selected time threshold serves as a time period during which the number and duration of pressure excursions above the threshold pressure level are used to perform an assessment. If warranted, the assessment concludes with an alarm (e.g., audible, visual, vibration, etc.) that alerts caregivers and, if possible, the patient so that the patient can be repositioned in a timely manner to avoid or at least reduce the risk of a pressure ulcer. The type and level of the alarm can be selected to induce conscious patients to move themselves in order to relieve the soft tissue pressure and stop the alarm, saving both tissue damage and the valuable time of a caregiver. As such, the monitoring system can also be viewed as a training device for patients who are cognitively aware and capable of repositioning themselves without assistance.

A significant feature of the invention outlined above is believed to be the correlation of pressure and time, combined with an alarm that is responsive to this correlation in order to reduce the likelihood that a patient will remain on fragile tissue or a pre-existing ulcer longer than is deemed to be clinically allowable. A preferred feature of the system is the ability to accurately detect soft tissue pressure above the threshold pressure level as detected by the pressure sensor embedded in the dressing assembly, monitor the duration over which the pressure is above this threshold, and then either sound the alarm if the pressure remains above the threshold for the preselected time period or reset the time period if the soft tissue pressure is adequately relieved before the preselected time period is exceeded.

The smart dressing is configured to hold a sensor adjacent to the skin of a patient may be removable from the dressing holder and replaceable, or may be affixed to or within the holder dressing. The holder dressing may have the sensor woven within it and it may have a space in which the sensor is irremovably fixed/incorporated. It may also have a measured space with a removable cover in which the sensor may be inserted and removed singly or on multiple occasions. Finally, it may be connected to a battery or sensor wires woven into the dressing.

The preferred embodiment of the current invention includes a dressing with a medical grade adhesive on one side of the dressing for adherence to the skin or other dressing. Preferably the adhesive will allow for multiple removal and reapplications. Additionally, the adhesive will be hypoallergenic and not damage skin. If the dressing is to be used for wound coverage, the dressing will have border adhesives and an absorbent foam/fabric against the open skin lesions. Soft silicone or hydrogel adhesives are preferred for these type of dressings.

The outer bed/chair surface may contain a removable portion to allow for introduction and removal of a sensor. In a preferred embodiment, the outer surface is a smooth tricot material eliminating friction and shear. A preferable version of the dressing allows for heat and humidity transfer.

The dressing surface facing the skin may be an adhesive foam/fabric for use over intact skin. In an alternate embodiment of the present invention, the dressing may also be a non-adhesive absorbent foam/fabric with a border adhesive. The dressing may further be comprised of a highly porous fabric for heat and moisture dissipation. It may also contain apertures for the imbedded sensor devices to actively/passively install medications.

The form and size of the dressing is based on which anatomic site it will be applied to and the sensor thickness. In the preferred embodiment of the current invention, at least three designs will be necessary although more may be found useful. The preferred dressing designs accommodate use with a patient's sacrum/coccyx, the heel/elbow, and the spine/outer hip/ischium areas with three corresponding circumferential sizes.

The thickness of the dressing/holder depends on the thickness of the sensor. A low density foam dressing in the present invention is two to three times the thickness of a rigid sensor to disseminate the focal pressure of the sensor to avoid skin pressure damage. Flexible printed circuit board sensors used in the preferred dressing are incorporated into thinner dressings. The foam density and dressing diameters also correspond to the thickness of the dressing.

The dressing in the preferred embodiment of the present invention includes an enclosure to hold and contain sensor devices capable of measuring vital signs including pressure, temperature, moisture, and HbO2, etc. and transmitting the monitored data wirelessly to outside mobile devices.

In particular, the inventive dressings are preferably of two thicknesses: one will be thinner (for example, 5 mm) of a soft padding like a foam with an appropriate adhesive on the bottom and an outer side opening for insertion and removal of the sensor, and an outer strip of adhesive to maintain the position of the sensor within the dressing. This dressing is to be applied over an existing wound dressing or directly onto the skin or wound area.

For sensors measuring vital elements, the sensor device dressing is placed on the skin so the sensor is separated from the skin by only a thin film adhesive. Thicker padding is placed over the sensor to disperse its pressure.

A second dressing includes an eight to ten millimeter thick foam dressing, for example a 4 mm thick dressing of a smaller circumference with an opening for the sensor, adhered to a larger circumference dressing that has an adhesive foam for adhering it to the skin/wound. The top/outer 4-5 mm portion holds the sensor, and is adherent to the skin contact 4-5 mm portion of dressing that is adherent to the skin or open wound. This skin surface types include:
1) Absorbent for moist open wounds and include an adhesive border as the absorbent portion may or may not be an adhesive.
2) A moist wound surface (for example Hydrogel) for dry wounds with an adhesive border.
3) An adhesive skin surface (for example Hydrogel/silicone adhesive) for contact to dry intact skin surfaces.

When the elements of the sensor can be reduced to less than two millimeter of thickness, the sensors are placed within a wider thin film dressing similar to a Bandaid dressing. This requires a wider larger area dressing to contain thin film batteries to power the Bluetooth Low Energy (BTLE) signals but forego the thicker foam padding portion of the dressings.

In the preferred embodiments of the present invention, all of the dressing variations described above require a very smooth tricot low friction outer water repellant cover to completely limit friction and shear forces from area. This outer cover would preferably be vapor and moisture permeable.

Yet another embodiment of the invention includes a disposable thin dressing (for example less than 2 mm thick) with printed circuit boards and battery power elements incorporated into the dressing fabrics for placement on the skin or wounds to measure a number of analog vital elements and the dressing includes power to transmit them to nearby mobile listening devices without the need for intervening bridges.

Numerous variations on the preferred embodiment of the sensor holding dressings include variations in adhesives between the skin and dressing, variation in the materials used for each layer of the dressing including variable foams, hyper absorbent fabrics, perforated breathable urethanes, etc., and variable use of border adhesives. Adhesive variations of acrylic, hydrogel, or silicone can be utilized. The ideal dressing of the preferred invention allows vapor and moisture transmission from the skin to the surface but protects the sensor elements.

Additionally, all different types of sensors may be used in the present invention including sensors monitoring pressure, temperature, moisture, capillary flow, skin resistivity and other biological indicators.

Figure 1:
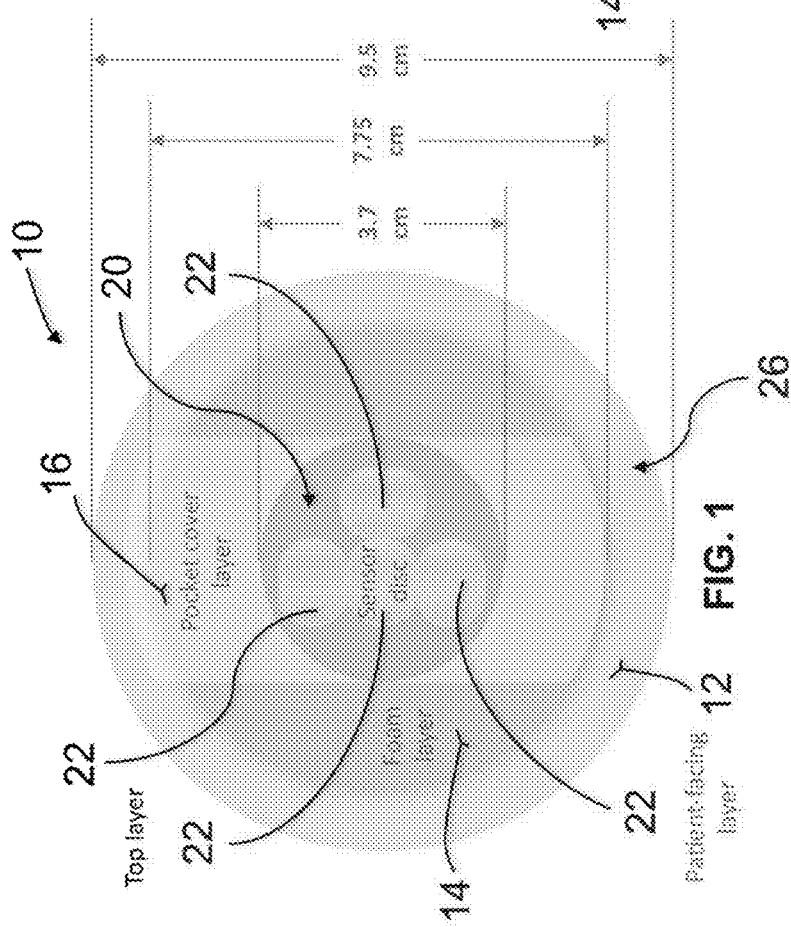
FIG. 1 schematically represents components of a dressing assembly in accordance with the preferred aspect of this invention.
Figure 3:
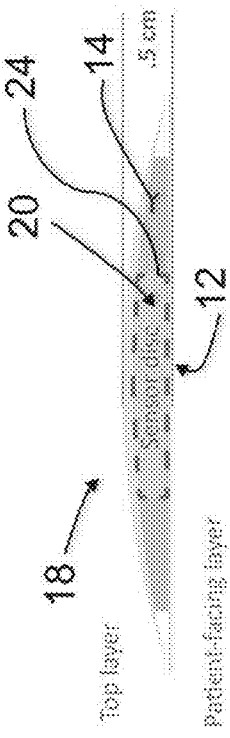
FIG. 3 schematically represents a side view of a dressing assembly in accordance with the preferred aspect of this invention.

FIGS. 1-3 represent a preferred embodiment of a pressure-sensitive dressing assembly 10 as shown in FIG. 1. In particular, the dressing assembly 10 in FIG. 1 has the ability to adhere directly to the skin or to an existing dressing. Therefore, dressing assembly 10 is not comprised of an adhesive that can damage the skin as is the case with acrylic. Dressing assembly 10 of the current invention is easily removed and reapplied as well. As a result, in the preferred embodiment of the current invention, dressing 10 has two versions of adhesives: hydrogel and soft silicon.

As illustrated in FIGS. 1-6, dressing assembly 10 has four primary layers in the present invention—a patient facing layer 12, a foam layer 14, a pocket cover layer 16 and a top layer 18 as illustrated in FIGS. 1-3.

Patient facing layer 12 is preferably a transparent film dressing of polymer (or other type of material) membrane with a thin coat of adhesive on one side. Patient facing layer 12 is impermeable to liquid, water and bacteria but permeable to moisture vapor and atmospheric gases to provide maximum flexibility. Patient facing layer 12 has one side with the reusable adhesive. The purpose of layer 12 is to attach the dressing to the skin of the patient or to attach dressing 10 to another dressing so that additional dressing layers can be attached directly to patient facing layer 12. There are multiple layers of material in the preferred embodiment of the current invention of dressing 10 wherein patient facing layer 12 is preferably the widest diameter layer amongst all of the layers in dressing 10.

Foam layer 14 is preferably a flexible plastic polymer (or other type of material) foam manufactured specifically for medical purposes so that a sensor assembly 20 comprised of one or more types of sensors 22 is not detected by the patient and sensor assembly 20 with sensors 22 do not negatively impact the patient's skin. In particular, in the preferred embodiment of the current invention, sensor assembly 20 does not negatively impact the patient's skin because pressure from sensors 22 within sensor assembly 20 distribute the pressure from sensors 22 on the patient across a larger area. Foam layer 14 includes a foam material with a strong adhesive and it adheres permanently to the film layer. The foam has an approximate thickness of 5 mm so that sensor 22 (which is approximately 3.8 mm) fits inside it with a back pad. The foam's length and width is smaller than patient facing layer 12.

Pocket cover layer 16 is preferably a film layer with a soft silicone or hydrogel adhesive. Pocket layer 16 adheres to foam layer 14 of dressing 10 and its purpose is to provide an opening/window for sensors 22 to be inserted and removed from foam layer 14. Pocket cover layer 16 is a soft adhesive layer with a thin soft foam pad (in the preferred embodiment of the present invention approximately 1.5-2 mm and collapsing to 1 mm when used) that covers the sensor pocket so that sensors 22 housed therein do not adhere to the top film. The opening/window soft adhesive needs to be larger than the sensor pocket so that pocket cover layer 16 can seal the pocket and also be opened and closed several times during use.

Top layer 18 is preferably a film with a strong adhesive. The purpose of top thin film 18 is to provide a very smooth low friction surface against the surface of the patient's bed or chair thereby preventing rolling of the dressing edges so that the dressing does not fall off of the patient. Top layer 18 also helps the other layers including patient facing layer 12, foam layer 14, and pocket cover layer 16 stay together in a tight configuration. Top layer 18 preferably has a very strong permanent adhesive. Top layer 18 has a cut out opening that outlines the pocket cover layer 16 for the removal and insertion of sensors 22.

Sensors 22 are housed within a pocket 24 formed within foam layer 14. In the preferred embodiment of the current invention, two different dressings include a round configuration 26 (FIGS. 1-3) and an oval configuration 28 (FIGS. 4-6). Round dressing assembly 26 is approximately 36 mm in diameter. Sensor pocket 24 corresponds to the shape of each sensor 22 so that there are two types of pockets. Each pocket 24 has an opening/window over sensor 22 so that sensor 22 can be removed from dressing assembly 10 and reapplied repeatedly. The adhesive on the sensor opening/window that connects to dressing assembly 10 is preferably comprised of a soft silicon or hydrogel and has a thin pad (preferably approximately 1 mm) that covers pocket 24 so that sensor 22 does not adhere to top film 18.

As illustrated in FIGS. 1-3, the thickness between top layer 18 and patient facing layer 12 of dressing assembly 10 in both the round (FIG. 3) and oval (FIG. 6) configurations is approximately 0.5 cm. Furthermore, it the round configuration, the diameter of the round configuration (FIG. 1) is approximately 9 cm while the oval configuration (FIGS. 4-5) is approximately 9 cm by 7 cm. Foam layer 14 in the round configuration is approximately 7 cm while foam layer in the oval configuration is approximately 5 cm wide by 7 cm long. Finally, pocket cover layer in the round configuration is approximately 3.7 cm×7.75 cm while in the oval configuration it is approximately 2.5 cm×6 cm.

As mentioned above, dressing assembly 10 may also integrate multiple different types of sensors including thermal, RBG, 3D, chemical, hyper spectral, accelerometer and situational awareness sensors.

As depicted in FIGS. 1-6, the preferred embodiment of dressing assembly 10 has many advantages including the ability to reuse sensors 22. Pocket 24 allows sensors 22 to be inserted and reused in a new dressing which saves the healthcare industry and patient money since they can reuse the same sensor for years.

Pocket 24 further protects the electronics from soiling and hurting patients since it includes a reusable adhesive that applies over and beyond the pocket area and pocket 24 has an additional foam cap 14 that protects it as well.

In the current invention, there is a snug fit around sensors 22 and the foam cap 14 permanently adhered to the flap over pocket 24 holds sensors 22 in place to ensure proper measurements are taken from the skin. It is critical to achieve this snug fit of holding the electronics board in place so it does not slip and injure the patient. Preferably a very strong but reusable adhesive and foam protector ensures sensors 22 stay in place against the patient's skin and do not fall out of pocket 24.

Reusable adhesive and extended trim allows patient facing layer 12 to be applied on top of an existing dressing and/or on different places on the body. It can also allow a caregiver to take it off and put the dressing back on during different bathing activities and to check the health of the skin.

Finally, top layer 18 facing a patient's bed and/or chair is smooth to allow very low friction on the bed and/or chair when the patient moves so that dressing assembly 10 does not peel off or the pocket flap over pocket 24 does not come off.

Dressing assembly 10 preferably is used to monitor soft tissue pressure at one or more surface regions of a patient's body that are susceptible to damage from soft tissue pressure. At least two pressure-sensitive sensors 22 in sensor assembly 20 are preferably provided to allow multiple areas of concern on the patient to be simultaneously monitored, though it is foreseeable that a single dressing assembly 10 may be sufficient under some circumstances. Dressing assemblies 10 are connected to a tablet, smartphone, computer, server or wireless converter through wireless connections. Dressing assemblies 10 may also be integrated into a patient's clothing, the bed or a large bed pad that covers a portion of the patient's bed.

As discussed above, sensors 22 in the preferred embodiment of the present invention alert a patient and/or a caregiver to a condition such as needing to move a patient, change a dressing or any other supportive activities to help the patient including bathing, changing a soiled diaper, or fall assistance.

FIGS. 4-6 illustrate an oval-shaped dressing assembly 10 with optionally vertically placed sensors 22. The oval geometry is provided for ideal placement on a heel or elbow to avoid a patient rolling onto dressing 10 causing false pressure vents when there is no pressure on it from the sensitive area. A round dressing 10 is not as well designed for this type of placement.

Figure 7:
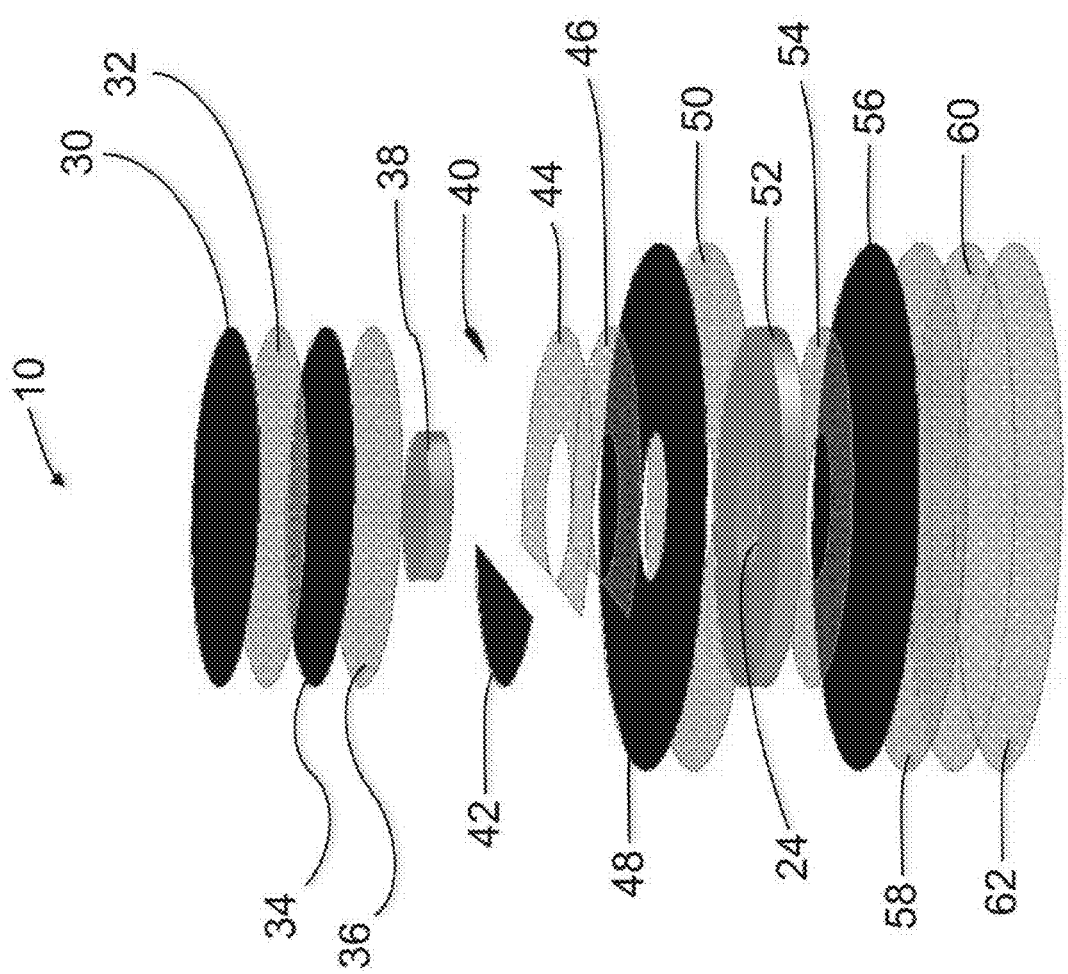
FIG. 7 represents an exploded view of a dressing assembly in accordance with the preferred aspect of this invention.

A more detailed view of the preferred embodiment of dressing assembly 10 is shown in FIG. 7. Dressing assembly 10 is configured to house sensor assembly 20 with sensors 22 within pocket 24. Sensors 22 are preferably dome sensors located on a printed circuit board (PCB).

Dressing sensor assembly 10 is adapted to generate electrical outputs corresponding to pressure, and particularly to soft tissue pressure to which sensors 22 are subjected to when placed on or near a patient's body. In order for dressing sensor assembly 10 to provide accurate pressure readings, a feature of the invention is the type of sensors used and their accuracy at the relatively low pressures of interest. While embodiments of the present invention have made use of variable output pressure sensors, including FlexForce® load sensors available from Tekscan, Inc., sensors comprising pressure-sensitive contacts have also been determined work well for use in dressing assembly 10 of this invention. In embodiments of sensors 22 utilizing a pressure-sensitive contact, for each occurrence in which the pressure sensed by sensor 22 exceeds the pressure threshold, an electrical contact will close and complete (short) an electrical circuit therein, causing sensor 22 to generate an identical output level regardless of what extent the soft tissue pressure may exceed the pressure threshold. The pressure-sensitive sensor 22 produces an electrical output signal generated by the completed electrical circuit that can be wirelessly transmitted to a tablet, smartphone, computer, server or wireless converter. If any one of the sensors 22 in the dressing assembly 10 exceeds the pressure threshold, the electrical output signal is preferably transmitted to the tablet, smartphone, computer, server or wireless converter to indicate a risk of an ulcer forming.

While the dressing assembly 10 is represented as comprising four sensors 22 in FIGS. 1-3 and two sensors 22 in FIGS. 4-6, it is within the scope of the invention for any one or more of the dressing assemblies 10 to comprise any number of sensors 22, which may promote the reliability and accuracy of the sensor readings from sensors 22. As non-limiting examples, two or more sensors 22 may be used to define a linear pattern, three or more sensors 22 may be used to define a triangular pattern, etc. Preferably, the dressing assembly 10 may also comprise a vibration device for alerting the patient to an alarm. Finally, it should be noted that the components of dressing assembly 10 may be constructed to be sufficiently thin to reduce pressure on and provide greater comfort for the patient. As described above, these components may include multi-layer thin film sensors, thin-film PCBs, thin-film batteries, etc.

In view of the foregoing, it should be apparent that the construction of sensors 22 largely determines the sensitivity and pressure threshold of dressing assembly 10. Though various configurations are possible, in practice suitable results have been obtained with the RK series of dome sensors commercially available from Snaptron, Inc. A particularly suitable dome sensor is believed to be part number RK50040, which is reported to have a maximum trip force (Fmax) of about 40 grams. In investigations leading to this invention, a 40 gram trip force applied to the RK50040 dome has been correlated to a minimum pressure level of about 32.5 mmHg (about 4330 Pa).

The construction of dressing assembly 10 preferably allows each dressing assembly to be applied and secured to a patient's body, such as to one or more bony prominences that are susceptible to damage from soft tissue pressure. The dressing assembly 10 may be located within a disposable sleeve that can be slipped over the dressing material to allow reuse of dressing assembly 10.

Referring to FIG. 7, preferably dressing assembly 10 includes a bloomer 30, a supported pressure sensitive adhesive (PSA) layer 32, a clear polyethylene (PE) layer 34, a second PSA layer 36, a foam layer 38, a high density polyethylene (HDPE) layer support 40, a third PSA layer 42, a second clear PE layer 44, a fourth PSA layer 46, a second bloomer 48, a fifth PSA layer 50, a second foam layer 52, a sixth PSA layer 54, a third bloomer 56, a seventh PSA layer 58, a silicone adhesive layer 60 and a fluoropolymer liner 62.

Bloomers 30, 48 and 56 provide a smooth surface so that the patient can slide around without any added friction. Transfer PSA layer 54 has a transfer tape that does not harbor a backing material. The pressure sensitive adhesive is coated onto the release liner and wound onto a roll. The release liner is always part of the transfer tape structure.

Pressure sensitive adhesive is an adhesive that forms a bond when pressure is applied to marry the adhesive with the adhered. No solvent, water or heat is needed to activate the adhesive. The PSA layers 32, 36, 42, 46, 50, 54 and 58 are designed to form a bond and hold properly at room temperature.

As illustrated in FIG. 7, HDPE support tab 40 adheres to third PSA layer 42 that forms a pocket flap over sensors 22. To replace a sensor, a user grabs onto support tab 40 to lift pocket flap layer 42 to expose sensor 22 in pocket 24. The use of sensor 22 being seated securely in pocket 24 that is accessible by opening flap 42 via tab 40 significantly minimizes peeling by patient movement. In particular, Tab 40 is constructed with a small smooth surface to avoid adhering to the adhesive so that a person can easily lift it up.

Figure 8:
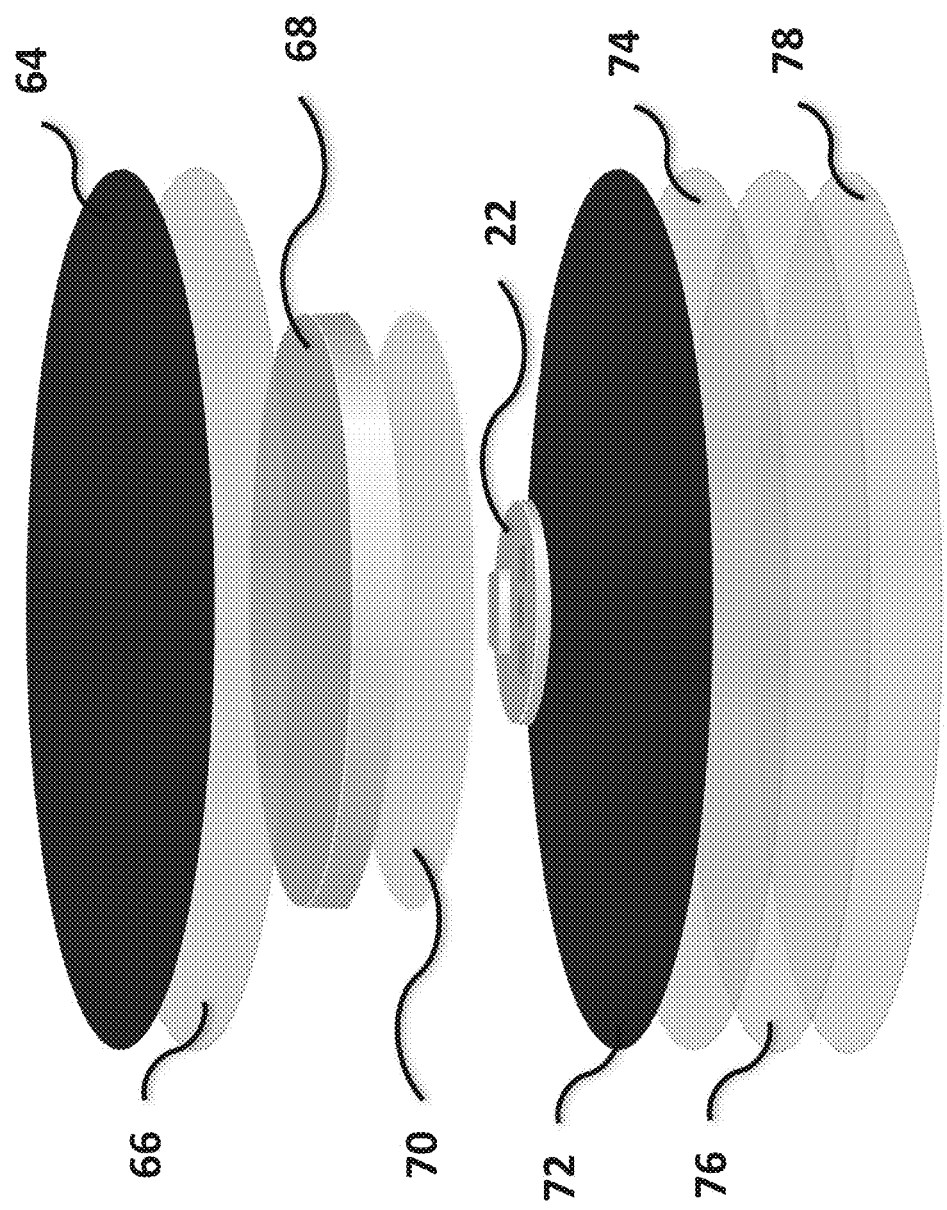
FIG. 8 schematically represents an alternative embodiment of a dressing assembly with a fixed sensor in accordance with an alternative embodiment of this invention.

FIG. 8 illustrates an alternative embodiment of dressing assembly 10 including a clear polyethylene (PE) layer 64, a PSA layer 66, a foam layer 68, a second PSA layer 70, a bloomer 72, a third PSA layer 74, a silicone adhesive layer 76 and a fluoropolymer liner 78. Sensors 22 are permanently disposed between second PSA layer 70 and bloomer 72.

Figure 9:
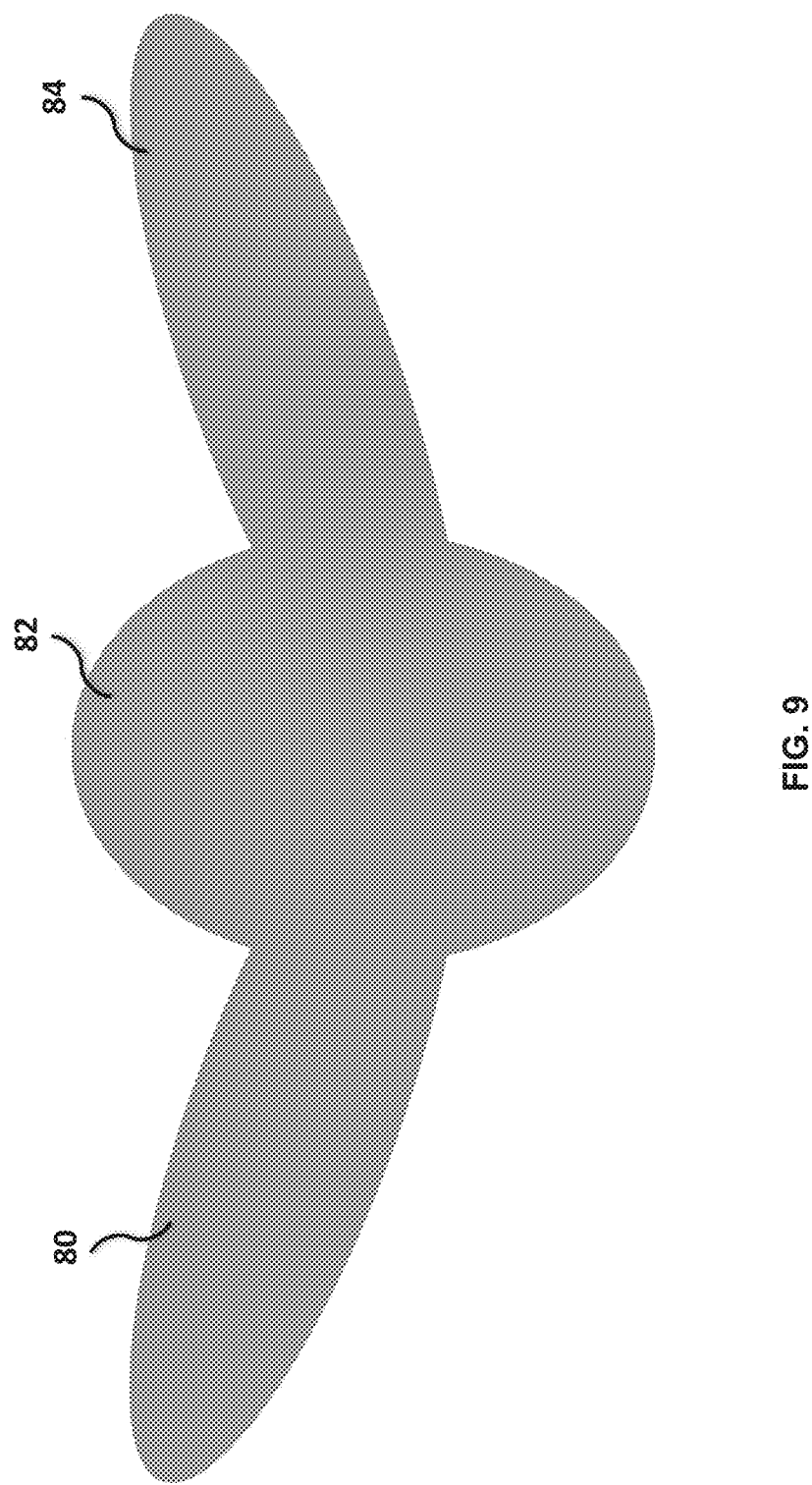
FIG. 9 schematically represents a dressing assembly for a heel in accordance with the preferred aspect of this invention.

FIG. 9 illustrates an alternative dressing assembly 10 designed for application on a heel of a patient. Assembly 10 includes a first flap 80 extending from an oval-shaped dressing portion 82. A second flap 84 disposed opposite first flap 80 cooperates with first flap 80 to secure dressing assembly 10 onto the heel of a patient. In particular, oval-shaped dressing portion 82 includes a bottom portion that is secured to the bottom of the patient's heel and an ankle support portion 84 that is wrapped around the ankle of the patient. After dressing 82 is placed on the heel and ankle of the patient, first flap 80 is wrapped around the front portion of the patient's ankle and second flap 84 overlaps first flap 80 and is affixed thereto by an adhesive surface to secure dressing 10 snugly around the heel and ankle of the patient.

First flap 80 and second flap 84 may alternatively be at various angles relative to oval-shaped dressing portion 82 to allow maximum flexibility for a patient to secure assembly 10 to the patient's heel. Additionally the lengths of flap 80 and flap 84 may also vary so that flaps 80 and 84 may not overlap one another but rather they may adhere directly to the patient's skin either on the top of the patient's foot or higher up around the patient's ankle depending on the lengths of flaps 80 and 84, and the angular disposition of flaps 80 and 84 relative to the oval-shaped dressing portion 82.

Figure 10:
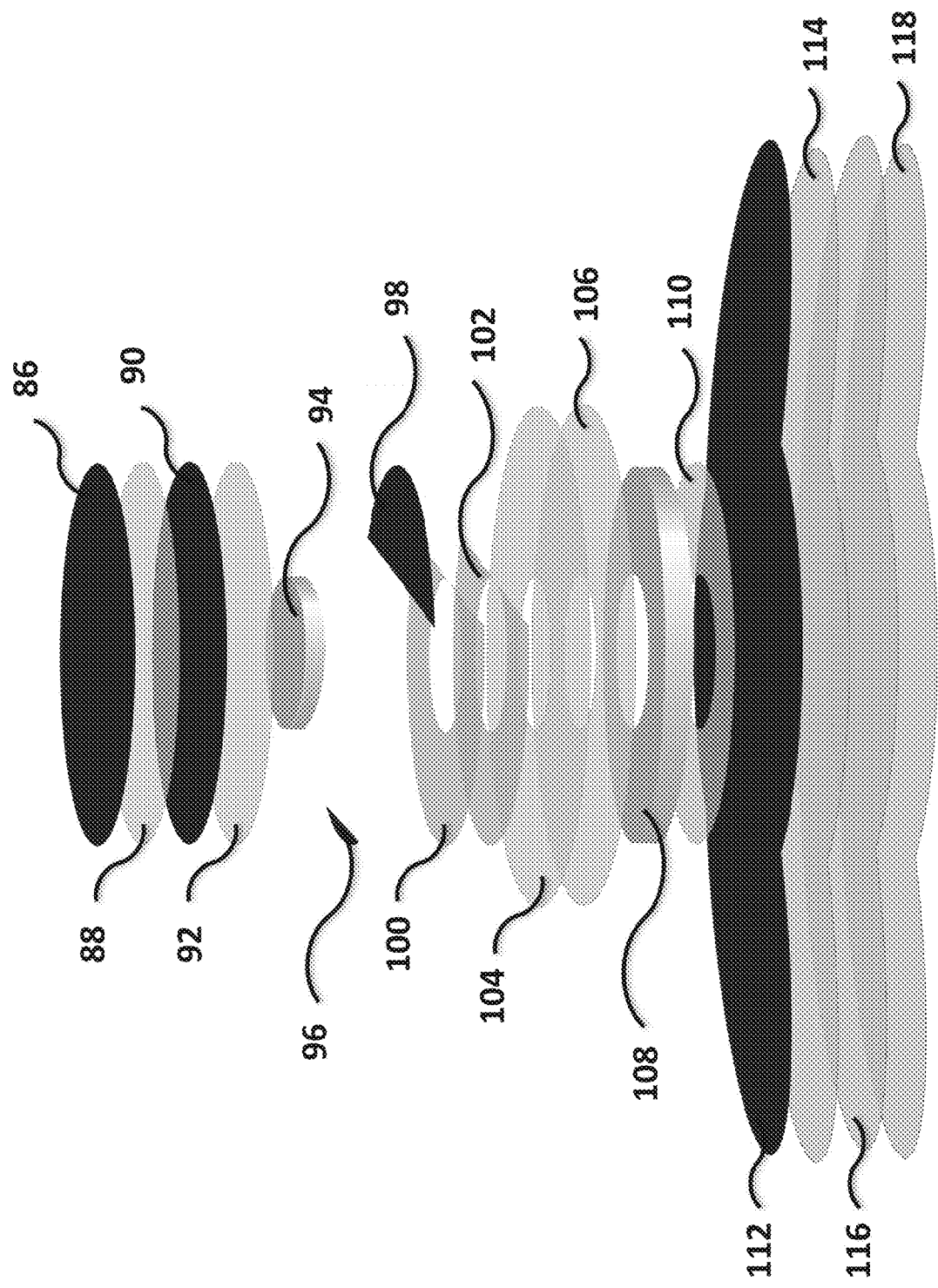
FIG. 10 schematically represents an exploded view of a dressing assembly for a heel in accordance with the preferred aspect of this invention.

As illustrated in FIG. 10, oval-shaped portion 82 of dressing 10 preferably includes a bloomer 86, a supported pressure sensitive adhesive (PSA) layer 88, a clear polyethylene (PE) layer 90, a second PSA layer 92, a foam layer 94, a high density polyethylene (HDPE) layer support 96, a third PSA layer 98, a second clear PE layer 100, a fourth PSA layer 102, a second bloomer 104, a fifth PSA layer 106, a second foam layer 108, a sixth PSA layer 110, a third bloomer 112, a seventh PSA layer 114, a silicone adhesive layer 116 and fluoropolymer liner 118.

Material for dressing assembly 10 is preferably provided so as to not interfere with any radio frequency signals with quality and/or strength of the signals. For example, some dressing in conventional hospitals included nickel to assist with faster healing of wounds, which may interfere with the wireless, smart dressing assembly 10 in the present invention.

Sensors 22 broadcast signals either periodically or based on an event. For example, sensors 22 may automatically broadcast messages including communicating a health indicator of the sensors. Sensors 22 may alternatively broadcast signals triggered by a particular ad hoc event or state change. The sensor data that is broadcast may relate to a variety of conditions including pressure, temperature, and/or moisture.

While the invention has been described in terms of specific embodiments, it is apparent that other forms could be adopted by one skilled in the art. For example, the dressing assembly and its components could differ in appearance and construction from the embodiment shown in the Figures, the functions of each component could be performed by components of different construction but capable of a similar (though not necessarily equivalent) function, and various materials and assembly, calibration and test procedures could be used in the manufacturing and setup of the dressing assembly 10. Other options include the use of different pressure measurement modalities (including variable output pressure sensors), and the use of any number of different geometric configurations of dressing assemblies 10 beyond an oval or a round configuration. Different sensor technologies can be incorporated into dressing assembly 10 to measure a range of specific pressures. As mentioned above, a variety of different sensors may be used to measure, among other things, temperature, pressure, moisture, capillary flow, skin resistivity and other biological indicators.

The system can also be configured for use by home patients and wheelchair patients, as well as for placement in the shoes of ambulatory patients to measure and warn against excess foot pressure-time. The system can also be adapted for use in treating pre-existing wounds and to incorporate wound care dressings into the dressing assembly 10, for example, by impregnating the dressing assembly with topical antibiotics to aid in the treatment of bacterial infected wounds. The system may additionally include temperature sensors to detect if the skin is increasing the probability of a PU for alerting and time. Moisture sensors could detect if the skin is increasing the probability of a PU for alerting and time as well.

A variable pressure sensor could assist in relating a patient's weight and other health factors when configuring alerts and alarms. The system could also detect if a patient was out of the bed or a seat if all sensors are not reading any pressure. The system could further include skin capillary stimulation if the skin is increasing the probability of a PU for alerting and time. The variable pressure sensor could detect softness and hardness of various beds and seats using a pressure sensor. A vibrator integrated into dressing assembly 10 could alert the patient as to which area is over pressure over time and needs to be relieved of pressure by moving away from the patient's current position.

Accordingly, it should be understood that the invention is not limited to the specific embodiments illustrated in the Figures. It should also be understood that the phraseology and terminology employed above are for the purpose of disclosing the illustrated embodiments, and do not necessarily serve as limitations to the scope of the invention. Finally, while the appended claims recite certain aspects believed to be associated with the invention, they do not necessarily serve as limitations to the scope of the invention.

The invention claimed is:

1. A dressing assembly for providing a warning to a patient or caregiver that the patient needs attention, the dressing assembly comprising:

a patient facing layer with an adhesive on a first side thereof that attaches the dressing assembly to the skin of a patient or to another dressing;

a foam layer overlying the patient-facing layer and having an opening therein that defines a pocket;

a pocket cover layer overlying the foam layer and releasably closing the pocket to enable access to the pocket, the pocket cover layer having a foam pad that protrudes into the pocket when the pocket cover layer releasably closes the pocket;

a top layer overlying the pocket cover layer; and at least a first sensor within the pocket, enclosed by the patient-facing layer, the foam layer, and the pocket cover layer, and held in place within the pocket by the foam pad, the first sensor generating electrical outputs corresponding to soft tissue pressure sensed by the first sensor at the surface of the patient's body.

2. The dressing assembly according to claim 1, wherein the at least one sensor is a wireless sensor.

3. The dressing assembly according to claim 1, wherein the adhesive on the patient facing layer is reusable.

4. The dressing assembly according to claim 1, wherein the pocket cover layer is configured to be lifted off the foam layer to access the pocket to insert and remove the at least one sensor therein.

5. The dressing assembly according to claim 1, wherein the at least one sensor comprises at least one electrically conductive dome sensor comprising conductive circuitry that are electrically shorted by the dome sensor if a predetermined pressure level is exceeded.

6. The dressing assembly according to claim 1, wherein the pocket cover layer is comprised of a silicone or hydrogel adhesive.

7. The dressing assembly according to claim 1, wherein the patient facing layer is impermeable to liquid, water and bacteria.

8. The dressing assembly according to claim 7, wherein the patient facing layer is permeable to moisture vapor and atmospheric gasses.

9. The dressing assembly according to claim 1, wherein the patient facing layer is oval-shaped.

10. The dressing assembly according to claim 9, wherein the patient facing layer further comprises a first ankle-wrapping flap extending therefrom and a second ankle-wrapping flap extending therefrom so as to be opposite the first ankle-wrapping flap.

11. The dressing assembly according to claim 1, wherein the pocket layer further comprises a tab secured thereupon for opening and closing the pocket cover layer.

* * * * *